United States Patent [19]

Nees et al.

[11] Patent Number: 4,667,044
[45] Date of Patent: May 19, 1987

[54] PROCESS FOR THE PRODUCTION OF AROMATIC GLYCIDYL ESTERS

[75] Inventors: Friedbert Nees, Stutensee; Peter Werle, Gelnhausen; Günther Reissmann, Aschaffenburg; Wolfgang Merk, Hanau, all of Fed. Rep. of Germany

[73] Assignee: Degussa Aktiengesellschaft, Frankfurt am Main, Fed. Rep. of Germany

[21] Appl. No.: 383,211

[22] Filed: May 28, 1982

[30] Foreign Application Priority Data

Jul. 4, 1981 [DE] Fed. Rep. of Germany ....... 3126411

[51] Int. Cl.$^4$ ............................................ C07D 301/00
[52] U.S. Cl. .................................... 549/539; 549/557
[58] Field of Search ........................................ 549/539

[56] References Cited

U.S. PATENT DOCUMENTS

| | | |
|---|---|---|
| 2,448,602 | 9/1948 | Kester et al. |
| 3,073,804 | 1/1963 | Raecke et al. |
| 3,301,920 | 1/1967 | Price ..................................... 549/539 |
| 3,454,531 | 7/1969 | Stewart . |
| 3,475,382 | 10/1969 | Stewart . |
| 3,576,827 | 4/1971 | Dukes et al. |
| 4,228,084 | 10/1980 | Ackermann et al. ............... 549/513 |
| 4,285,872 | 8/1981 | Tanabe et al. ...................... 549/513 |

FOREIGN PATENT DOCUMENTS

| | | |
|---|---|---|
| 0008112 | 2/1980 | European Pat. Off. . |
| 1030824 | 5/1958 | Fed. Rep. of Germany . |
| 1081013 | 5/1960 | Fed. Rep. of Germany . |
| 1082263 | 5/1960 | Fed. Rep. of Germany . |
| 2126280 | 12/1971 | Fed. Rep. of Germany . |
| 1643777 | 6/1972 | Fed. Rep. of Germany . |
| 2107084 | 9/1972 | Fed. Rep. of Germany . |
| 2602157 | 7/1976 | Fed. Rep. of Germany . |
| 2654306 | 6/1977 | Fed. Rep. of Germany . |
| 862588 | 3/1961 | United Kingdom . |

OTHER PUBLICATIONS

F. Zetzsche et al., Helv. Chim. Acta, vol. IX (1926) pp. 708–714.
Hao et al., Die Angewandte Makromolekulare Chemie, vol. 31(443,) (1973), pp. 83–113.
S. R. Sandler et al., Journal of Chemical and Engineering Data, vol. 11(3), Jul. 1966, pp. 447–448.
H. Zondler et al., Helv.Chim.Acta, vol. 60, Fasc. 6 (1977)–No. 181, pp. 1845–1860.
Chem. Abst. vol. 94, No. 17, p. 744, No. 139598k.

*Primary Examiner*—Norma S. Milestone
*Attorney, Agent, or Firm*—Cushman, Darby & Cushman

[57] ABSTRACT

Aromatic mono or polycarboxylic acid glycidyl esters are obtained in good yields and high purity by transesterification of the corresponding aromatic carboxylic acid alkyl esters with glycidol in the presence of weakly toxic catalysts, namely the alkali, ammonium, and alkaline earth metal salts of pseudohalogen hydride acids with readily polarizable anions.

22 Claims, No Drawings

PROCESS FOR THE PRODUCTION OF AROMATIC GLYCIDYL ESTERS

BACKGROUND OF THE INVENTION

Glycidyl esters of aromatic carboxylic acids can be employed in many ways in the adhesive, synthetic resin and lacquer industries and have been claimed as crosslinking components, e.g., in diverse patents for the production of heat-hardenable coating compositions.

Additionally, there are known several methods for the production of these compositions. As is mentioned in Hao, Die Angewandte Makomolekularen Chemie Vol. 31, pages 83–113 (1973), glycidyl esters can be produced by:

1. Reaction of epichlorohydrin with carboxylic acids and subsequent dehydrohalogenation Japanese application No. SHO 55-127380 U.S. Pat. No. 3,576,827, German AS No. 2,126,280, German AS No. 1,643,777.
2. Reaction of epichlorohydrin with salts of carboxylic acids, Hao, Die Angewandte Makromolekularen Chemie Vol. 31 (1973), pages 83–113 (No. 443).
3. By epoxidation of allyl esters, EPO published application No. 0008,112.
4. By reaction of acid chlorides with 2,3epoxypropanol (glycidol), Sandler, J. Chem. Eng. Data Vol. II, No. 3, pages 447–448.

Furthermore, there may be mentioned the following possibilities described in the literature.

5. Reaction of an acid hydride with epichlorohydrin.
6. Transesterification of acid esters with glycidyl esters, German OS No. 2107084.
7. Transesterification of acid esters with glycidol, Russian patent No. 405,880, German OS No. 2,602,157.

All described methods up to now are neither suited for large scale manufacture or are associated with various disadvantages which affect the quality of the end product.

The dehydrohalogenation of the 2,3-hydroxychloropropyl esters, which are obtained by reaction of the carboxylic acid with epichlorohydrin, with an alkaline reagent (e.g., German AS No. 1,030,824 and Dukes U.S. Pat. No. 3,576,827) or by re-epoxidation with further epichlorohydrin (German AS No. 1,643,777 and German AS No. 2,126,280) in the first case with mild reaction conditions does not lead to complete splitting off of Cl, but with stronger conditions leads to a breaking of the ester bond so that the glycidyl ester formed again splits off (see German AS No. 1,030,824). In the second case, as generally is the case in the reaction with epichlorohydrin, it is not possible to arrive at chloride free end products, the process produces as is the case with the reaction of carboxylic acid anhydride with epichlorohydride (Japanese application SHO 55-127380 large amounts of organic loaded salt.

Besides, all of the mentioned processes are expensive in their industrial application because the reaction of the alkali salt with epichlorohydrin (e.g., German patent No. 1,081,013 and Kester U.S. Pat. No. 2,448,602) brings about no substantial advantages, especially since a further process step is needed, namely the production of the carboxylic acid salt involved. The content of residual chlorine in all the processes is quite high and can amount to several percent. The epoxidation of the allyl ester with per compounds is mentioned in several patents (see, e.g., Great Britain patent No. 862,588, German AS No. 1,082,263, S. R. Sandler and F. R. Berg, J. Chem. and Eng. Data, Vol. 11, pages 447–448 (1966) and European published application No. 0008112).

Until now, these methods have only been used to a limited extent since the processes are expensive and technologically difficult. The reaction of acid chlorides with glycidol because of the poor availability of the chloride and the high accumulation of alkali or amine salts brings no advantages in regard to quality and simplicity of the course of the reaction (see, e.g., F. Zetche and F. Aeschlimann, Helv. Chim. Acta Vol. 9, pages 708–714 (1929), Raecke U.S. Pat. No. 3,073,804).

The transesterification of acid esters with lower molecular weight aliphatic glycidyl esters (German OS No. 2,654,306 and German OS No. 2,107,084) is indeed possible, but the process fails for large scale manufacture because of the poor availability of the aliphatic glycidyl esters.

Glycidyl esters can also be produced by reaction of glycidol with esters of aromatic carboxylic acid, preferably the methyl esters.

This process is technically elegant and of little expense in regard to the apparatus and working up of the mother liquor. Besides, the necessary starting components are available on an industrial scale.

Until now, there has only unsatisfactorily been solved the question of usable catalysts. In the USSR patent No. 405,880, there is claimed zinc acetate. However, the stated reaction temperatures of 100°–150° C. led to a quick polyaddition of the glycidol. In reworking the stated process, there were always obtained only small amounts of diglycidyl ester, besides much starting product, there was ascertained a considerable polymer portion.

Zondler et al describe in Helv. Chim. Acta. Vol. 60, pages 1845–1860 (1977), as well as in the German OS No. 2,602,157, the transesterification of carboxylic acid methyl esters with glycidol in the presence of different thallium salts as catalysts.

Their investigations of the systems HgO, CdO, PbO, $PbO_2$, $Sb_2O_3$, $Bi_2O_3$, $Ga_2O_3$, $In_2O_3$, $Mn(ac)_2$, $Hg(ac)_2$, $Pb(ac)_2$, $UO_2(ac)_2$, $TiO(acac)_2$, $In(acac)_3$, $Th(acac)_4$, $Ga(O-n-C_4H_9)_4$, $Ti(O-n-C_4H_9)_4$, $Ti(O-iso-C_3H_7)_4$, $(n-C_4H_9)Sn(ac)_3$, $(n-C_4H_9)_3Si-ac$, $n-C_4H_9-Sn-OOH$ and KCN show that all catalysts show no or little activity below 100° C. Therefore, there results only low degree of reaction.

The thallium containing catalysts such as $TlNO_3$, $Tl_2O_3$, $TlOCOCH_3$ among others claimed in the above German Offenlengungsschrift indeed show a good activity, but it is practically not possible to isolate the glycidyl ester formed in thallium free form. Because of the known toxicity of this metal and its derivatives, the employment of such thallium containing esters is greatly limited.

The invention, therefore, is based on the problem of finding catalysts for the technically simple process of transesterification of methyl esters with glycidol which permits the production of glycidyl esters on a large scale because of their activity and low toxicity.

Precisely, the transesterification of polybasic carboxylic acid esters is a problem since it concerns further reacting the product of the intermediately occurring intermediate step, i.e., the mixed ester in the direction of the pure glycidyl ester. The catalysts used for the reaction of monoesters are not suited without doing anything else for reacting polyester. Rather, it has been shown that the catalysts claimed for aromatic carboxylic acid monoesters such as NaOCH₃ (German OS No.2,107,084), other basic materials such as hydroxides or cyanides, ion exchangers, acids such as H₂SO₄, p-toluenesulfonic acid are not suited to produce pure polyglycidyl esters.

The reaction with glycidol many times only leads to the formation of the monoglycidyl ester, e.g., there is obtained in the transesterification of dimethyl terephthalate with 2 moles of glycidol in the presence of KCN chiefly the monoester, besides the starting product and much polymeric material.

A large number of alkali salts which were examined in regard to the catalytic activity proved to be not suited. There belongs to this group among others the anions of the following acids:

$PO_4^{3-}$, $HCO_3^-$, $HPO_4^{2-}$, $NO_3^-$, $NO_2^-$, $BO_2^-$, $H_2PO_2^-$, $BH_3CN^-$, $SO_4^{2-}$, $SO_3^{2-}$, $IO_4^-$, $S_2O_8^{2-}$, $S_2O_5^{2-}$, $S_2O_4^{2-}$.

The problem of the process of the invention, therefore, is to produce aromatic mono, and above all polycarboxylic acid glycidyl esters by reaction of aromatic carboxylic acid alkyl esters with glycidol in very good yields and high purity, namely using environmentally favorable catalysts.

SUMMARY OF THE INVENTION

It has now been found that the transesterification of aromatic mono and polycarboxylic acid alkyl esters to the corresponding glycidyl esters can be carried out with glycidol industrially in a simple manner if the known transesterification is carried out with so-called pseudohalogen hydrides which have an easily polarizable anion.

Under the term "pseudohalogen hydrides" which have an easily polarizable anion are understood, e.g.:

Alkali metal salts of hydrazoic acid HN₃, cyanic acid HOCN, fulminic acid HONC, thiocyanic acid HSCN, selenocyanic acid HSeCN, tricyanomethamide HC(CN)₃, dicyanimide HN(CN)₂, as well as cyanamide H₂NCN also.

As alkali metal salts, above all there are considered Li, Na, and K, in some cases also NH₄, e.g. lithium cyanate, ammonium thiocyanat.

Preferred are the sodium and potassium salts. Especially preferred are sodium azide, potassium cyanate, and sodium dicyanimide.

The alkali salts of the named pseudohalogen hydrides are stable at room temperature.

There can also be employed the alkaline earth metal salts, e.g., calcium salts, e.g., calcium cyanate, if their solubility in the reaction medium is sufficient; also, there can be employed alkali carbonate or thiosulfate, e.g., sodium carbonate, potassium carbonate, sodium thiosulfate, or potassium thiosulfate.

The catalysts used according to the invention can be employed in amounts at will, inter alia, however, amounts of 0.001–0.01 mole per mole of carboxylic acid alkyl ester are sufficient, preferred amounts are 0.002–0.004 mole per mole of carboxylic alkyl ester.

An advantage of the process of the invention is in the possibility of carrying out the transesterification at relatively low temperatures, i.e., at about 50°–80° C. Preferred is a temperature of 60° C.

Therefore, there can also be used the alkali metal and alkaline earth metal salts of fulminic acid.

If the aromatic carboxylic acid esters are completely soluble in glycidol, the transesterification can be carried out without a solvent; however, a solvent can be employed.

As solvents, there can be used, for example, aromatic hydrocarbons such as benzene, toluene, xylene, trimethyl benzene, as well as their chlorinated derivatives, e.g., chlorobenzene, dichlorobenzene, p-chlorotoluene, o-chlorotoluene, as well as all solvents in which the components of the transesterification can be dissolved and which are inert to these components.

Preferred solvents are toluene and xylene. Inter alia, polymerization inhibitors are not necessary.

Especially suited among the aromatic mono and polycarboxylic acids are benzoic acid, benzene di, tri, and tetracarboxylic acids, e.g., ortho phthalic acid, isophthalic acid, terephthalic acid, trimesic acid, trimellitic acid, and pyromellitic acid, toluic acid, 1,8-naphthalene carboxylic acid, 2,5-dimethyl terephthalic aid, 2,6-naphthalene dicarboxylic acid, 2,3-naphthalene dicarboxylic acid, hemimellitic acid, benzene-1,2,3,4-tetracarboxylic acid, naphthalene tetracarboxylic acid, perylene tetracarboxylic acid, diphenyl-4,4-dicarboxylic acid.

Preferred are benzoic acid, benzene tricarboxylic acids, especially trimesic acid, the phthalic acids, and among these, especially terephthalic acid.

As alkyl esters of the aromatic carboxylic acids, there can be used those with lower alcohols such as methyl and ethyl ester. Methyl esters are preferred.

Examples of esters are dimethyl terephthalate, diethyl terephthalate, dimethyl phthalate, dimethyl isophthalate, trimethyl trimesate, methyl benzoate, methyl toluate.

Glycidol is used in commercial form.

The transesterification is carried out under normal pressure. However, if required increased or lowered pressure can also be used, in any case the alcohol formed, for the most part methanol, is removed from the reaction mixture. In using normal pressure, for this purpose there is then needed reduced pressure.

The aromatic carboxylic acid ester and glycidol can be employed in stoichiometric amounts, inter alia, however, a slight excess of glycidol of about 0.1–0.2 moles of glycidol per mole of carboxyl group is suitable.

The reaction time, inter alia, is 5–7 hours. The end of the reaction is detected by thin layer chromatography.

The isolation of the product takes place by distillation off of the solvent or the greatest possible concentration with subsequent crystallization. Generally, a further crystallization is not necessary, since the glycidyl ester produced according to the process has high purity and high epoxide content.

The technical advance of the process of the invention is first in the very good yields, besides also in the great purity of the transesterification products. Above all, this also is correct for so-called mixed esters of multibasic carboxylic acids where two or more carboxyl groups not only contain glycidyl residues, but also the alkyl groups of the aromatic carboxylic acids employed.

Furthermore, the transesterification catalysts used in the invention are only weakly toxic.

Unless otherwise indicated, all parts and percentages are by weight.

The process can comprise, consist essentially of, or consist of the stated steps with the recited material.

The following examples explain the invention in more detail.

DETAILED DESCRIPTION

Apparatus:

On a 250 ml, three neck flask having an inner thermometer, there is located a packed column about 20 cm long to which there is connected an intensive condenser heated to 40° C. This is joined to a bent piece having a thermometer, to which there is connected a discending spiral condenser which is cooled with water, as well as an alternating vacuum receiver, e.g , according to Anschütz-Thiele. On the alternating vacuum receiver, there is located a flask in an ice-bath.

The components, together with xylene, were filled into the flask and heated to 60° C. By applying a vacuum (about 60–70 mbar), the methanol split off was evaporated and driven out of the reaction space into the receiver. The end of the reaction was detected by thin layer chromatographic analysis with silica gel plates for thin layer chromatography in a running agent system acetone/hexane 1:3 on the disappearance of the starting and intermediate ester.

EXAMPLE 1

17 grams (0.125 mole) of methyl benzoate and 10.6 grams (0.143 mole) of glycidol in 100 ml of xylene were caused to react by 0.07 grams ($4.9 \times 10^{-4}$ mole) of KSeCN at 60° C. After about 5 hours, the reaction was ended. The crude yield of colorless glycidyl benzoate amounted to 21.6 grams (97% of theory based on the methyl benzoate), Epoxide content 96.2%.

EXAMPLE 2

24.25 grams (0.125 mole) of dimethyl terephthalate (DMT), 21.3 grams (0.287 mole) of glycidol, 100 ml of xylene, as well as 0.03 gram ($4.9 \times 10^{-4}$ mole) of sodium azide were treated for 6–7 hours at 60° C. in a manner analogous to Example 1.

After the distillation off of the xylene, there remained 46.2 grams (97.7% of theory based on DMT) of colorless diglycidyl terephthalate having an epoxide content of 96%.

EXAMPLE 3

The procedure was as in Example 2, except as catalyst there was used 0.03 gram ($4.9 \times 10^{-4}$ mole) of $NaN(CN)_2$. Yield of diglycidyl terephthalate 94.8% of theory, epoxide content 94.1%.

EXAMPLE 4

The procedure was as in Example 2, except that there were employed only 0.015 gram ($2.5 \times 10^{-4}$ mole) of sodium azide. Yield 96.3% of theory, Epoxide content 95.3%.

EXAMPLE 5

31.5 grams (0.125 mole) of trimethyl trimesate, 32 grams (0.43 mole) of glycidol, and 0.04 gram ($4.9 \times 10^{-4}$ mole) of potassium cyanate were treated in the manner described in Example 2. The crude yield was 46.2 grams (97.7% of theory based on the starting ester), Epoxide content 96.7%.

What is claimed is:

1. In a process for the production of a glycidyl ester of an aromatic mono or polyoarboxylic by reacting an alkyl ester of an aromatic carboxylic acid with glycidol, the improvement comprising carrying out the reaction in the presence of a catalytically effective amount of an alkali metal, ammonium, or alkaline earth metal salt of hydrazoic acid, cyanic acid, fulminic acid, thiocyanic acid, selenocyanic acid, tricyanomethamide, dicyanimide or cyanamide.

2. A process according to claim 1 wherein the salt is an alkali metal salt.

3. A process according to claim 1 wherein the catalyst is used in an amount of 0.0001 to 0.01 mole per mole of alkyl ester of the aromatic carboxylic acid.

4. A process according to claim 3 wherein the catalyst is used in an amount of 0.002 to 0.004 mole per mole of alkyl ester of the aromatic carboxylic acid.

5. A process according to claim 4 wherein the catalyst is sodium azide, sodium cyanimide, potassium cyanate, or potassium selenocyanate.

6. A process according to claim 3 wherein the catalyst is sodium azide, sodium cyanimide, potassium cyanate, or potassium selenocyanate.

7. A process according to claim 1 wherein the alkyl ester is methyl benzoate.

8. A process according to claim 7 wherein the catalyst is used in an amount of 0.0001 to 0.01 mole per mole of alkyl ester of the aromatic carboxylic acid.

9. A process of claim 8 wherein the temperature is 50°–80° C.

10. A process according to claim 9 wherein the catalyst is sodium azide, sodium cyanimide, potassium cyanate, or potassium selenocyanate.

11. A process according to claim 1, wherein the alkyl ester is a methyl ester of a benzene dicarboxylic acid, benzene tricarboxylic acid, or benzene tetracarboxylic acid and all of the alkyl groups are replaced by glycidyl groups.

12. A process according to claim 11 wherein the catalyst is used in an amount of 0.0001 to 0.01 mole per mole of alkyl ester of the aromatic carboxylic acid.

13. A process according to claim 12 wherein the temperature is 50°–80° C.

14. A process according to claim 13 wherein the catalyst is sodium azide, sodium cyanimide, potassium cyanate, or potassium selenocyanate.

15. A process according to claim 8 wherein the alkyl ester is dimethyl phthalate, dimethyl isophthalate, or dimethyl terephthalate.

16. A process according to claim 15 wherein the catalyst is used in an amount of 0.0001 to 0.01 mole per mole of alkyl ester of the aromatic carboxylic acid.

17. A process according to claim 16 wherein the temperature is 50°–80° C.

18. A process according to claim 17 wherein the catalyst is sodium azide, sodium cyanimide, potassium cyanate, or potassium selenocyanate.

19. A process according to claim 18 wherein the ester is dimethyl terephthalate.

20. A process according to claim 15 wherein the ester is dimethyl terephthalate.

21. A process according to claim 11 wherein the ester is trimethyl trimesate.

22. A process according to claim 21 wherein the temperature is 50°–80° C. and wherein the catalyst is sodium azide, sodium cyanimide, potassium cyanate, or potassium selenocyanate.

* * * * *

UNITED STATES PATENT AND TRADEMARK OFFICE
CERTIFICATE OF CORRECTION

PATENT NO. : 4,667,044
DATED : May 19, 1987
INVENTOR(S) : Nees et al

It is certified that error appears in the above—identified patent and that said Letters Patent is hereby corrected as shown below:

Claim 1, line 2, change "polyoarboxylic" to --polycarboxylic--.

Signed and Sealed this

Seventeenth Day of November, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,667,044
DATED : May 19, 1987
INVENTOR(S) : Nees et al

It is certified that error appears in the above-identified patent and that said Letters Patent is hereby corrected as shown below:

Claim 1, line 2, "polyoarboxylic" should read
-- polycarboxylic acid --.

This certificate supercedes Certificat of Correction issued November 17, 1987.

Signed and Sealed this

Fifth Day of January, 1988

Attest:

DONALD J. QUIGG

Attesting Officer

Commissioner of Patents and Trademarks